US00PP11563P

United States Patent [19]

Walden

[11] Patent Number: Plant 11,563

[45] Date of Patent: Oct. 10, 2000

[54] GROUNDCOVER SHRUB ROSE PLANT NAMED 'JACGRON'

[75] Inventor: John K. Walden, Thousand Oaks, Calif.

[73] Assignee: Bear Creek Gardens, Inc., Medford, Oreg.

[21] Appl. No.: 09/227,039

[22] Filed: Jan. 7, 1999

[51] Int. Cl.[7] ..... A01H 5/00

[52] U.S. Cl. ..... Plt./102

[58] Field of Search ..... Plt./101, 102, 107, Plt./116, 123, 141

*Primary Examiner*—Howard J. Locker

*Attorney, Agent, or Firm*—Klarquist Sparkman Campbell Leigh & Whinston, LLP

[57] ABSTRACT

A groundcover shrub rose plant having a low-growing, spreading growth habit; recurrent bloom habit; dark green, glossy foliage; and resistance to the diseases of rose rust, rose powdery mildew, and blackspot.

1 Drawing Sheet

The present invention relates to a new and distinct variety of rose plant of the groundcover shrub rose plant class which was originated by me by crossing the variety 'JAClover', U.S. Plant Pat. No. 9324, with the variety 'JACcasp', U.S. Plant Pat. No. 8719.

The primary objective of this breeding was to produce a new rose variety having a low growing, spreading ground cover plant habit; recurrent bloom habit; dark green, glossy foliage; and resistance to rose rust, rose powdery mildew, and blackspot. The objective was substantially achieved, along with other desirable improvements, as evidenced by the following unique combination of characteristics that are outstanding in the new variety and that distinguish it from its parents, as well as from all other varieties of which I am aware:

1. Low, spreading, groundcover plant habit;
2. Resistance to rose rust, blackspot, and powdery mildew;
3. Simple five-petaled, pink and white flower;
4. Dark green, glossy foliage; and
5. Rapid repeat bloom cycle.

Asexual reproduction of this new variety by cuttings and budding as performed at Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JAClover', U.S. Plant Pat. No. 9324.

*Pollen parent.*—'JACcasp', U.S. Plant Pat. No. 8719.

Classification:

*Botanical.*—*Rosa hybrida.*

*Commercial.*—Groundcover shrub rose.

FLOWER

Observations made from specimens grown in a garden environment at Wasco, Calif. on Nov. 25, 1998.

Blooming habit.—Recurrent.

Bud:

*Size.*—About ⅜ to ½ inch long when the petals start to unfurl.

*Form.*—The bud form is short, pointed ovoid.

*Color.*—When sepals first divide, bud color is near Red Group 46A on outer one-half of petal, and Yellow Group 4D on inner one-half of petal. When half blown, the upper sides of the petals are near Red Group 46A at petal edges, mixing with White Group 1 55A toward the bottom two-thirds of petals, terminating at the petal bases in Yellow Group 4D; and the lower sides of the petals are near Red Group 46A at petal edges, mixing with White Group 1 55A on the bottom two-thirds of the petal.

*Sepals.*—Color: Near Yellow-Green Group 144A. Surface texture: Rough, glandular. There are three lightly appendaged sepals. There are two unappendaged sepals with moderately hairy edges.

*Receptacle.*—Color: Yellow-Green Group 144A. Shape: Funnel. Size: Small, about 3/16 inch×3/16 inch. Surface: Glandular.

*Peduncle.*—Length: Short, about ¾ inches. Surface: Rough, glandular. Color: Light green (Yellow-Green Group 146C). Strength: Stiff, slender.

Bloom:

*Size.*—Small. Average open size is 1½ inches.

*Borne.*—Singly and in clusters having rounded shape.

*Stems.*—Short, average length is about four to six inches.

*Form.*—When first open: Flat. Permanence: Outer petal edges curl slightly.

*Petalage.*—Number of petals under normal conditions: Five.

*Color.*—The upper sides of the petals are Red Group 53C mixed with White Group 155D on the outer one-half of the petal with concentration of Red Group 53C along mid-vein of petal, and the inner one-half of the petal is White Group 155A. The reverse sides of the petals are near Red Group 56D mixed with Red Group 51 B near petal edges. The base of each petal has a small spot of Yellow-Orange Group 14D at point of attachment. The major colors on the upper sides are Red Group 53C and White Group 155D.

*Discoloration.*—The general tonality at the end of the first day: unchanged. At the end of the third day: Color on upper sides is Red Group 56B and White Group 155D.

*Fragrance*.—None.

Petals:

*Texture*.—Thin.

*Shape*.—Oval.

*Form*.—Tips slightly recurved.

*Arrangement*.—Regularly arranged. Petaloids in the center: None.

*Persistence*.—Petals drop off cleanly before drying.

*Lastingness*.—On the plant: Fair (about seven days). As a cut flower: Not tested.

Reproductive parts:

*Anthers*.—Size: Medium. Quantity: Many. Color: Yellow, near Yellow-Orange Group 21A. Arrangement: Regular around styles.

*Filaments*.—Color: Pale yellow (Yellow Group 4D).

*Pollen*.—Color: Gold-yellow (Yellow-Orange Group 21C.)

*Styles*.—Color: Near Yellow-Green Group 145D.

*Stigmas*.—Color: Greenish-white (Green-White Group 157C).

Plant:

*Form*.—Shrub, groundcover.

*Growth*.—Very vigorous, branching, sprawling. At maturity, height is 1 foot, width is 6½ feet.

Foliage: Number of leaflets on normal mid-stem leaves: Seven.

*Size*.—Small, about 2¾ inches long ×1⅜ inches wide.

*Quantity*.—Normal.

*Color*.—New foliage: Upper surfaces: Near Yellow Green Group 146A; lower surfaces Greyed Red Group 178A, rapidly turning green. Old foliage: Upper surfaces: Near Green Group 139A. Lower surfaces: Yellow-Green Group 147B.

Leaflets:

*Shape*.—Pointed oval.

*Texture*.—Glossy, smooth.

*Edge*.—Serrated.

*Serration*.—Single.

*Petiole rachis*.—Color: Green, between Green Group 137B and 137C.

*Petiole underside*.—With prickles.

*Stipules*.—Medium (about ½ inch).

*Disease resistance*.—to rust, mildew and blackspot under normal growing conditions at Somis and Wasco, Calif.

Wood:

*New wood*.—Color: Yellow-Green Group 144B with overlay of Greyed-Red Group 178B. Bark: Smooth.

*Old wood*.—Color: Green Group 146B. Bark: Smooth.

Prickles:

*Quantity*.—On main canes from base: Ordinary to few. On laterals from main canes: Ordinary to few.

*Form*.—Medium, hooked downward.

*Color when young*.—Red, between Greyed-Red Group 178A and 178B.

*Color when mature*.—Near Greyed-Yellow Group 162D.

Small prickles:

*Quantity*.—On main stalks: None. On laterals: Few: On new wood, especially from basal shoots, there are both prickles and numerous small prickles. The small prickles fall away as the wood matures.

*Color*.—Between Greyed-Red Groups 178A and 178B.

I claim:

1. A new and distinct variety of rose plant of the groundcover shrub rose class, substantially as herein shown and described, characterized particularly by its low-growing, spreading growth habit; recurrent bloom habit; dark green, glossy foliage; and resistance to the diseases of rose rust, rose powdery mildew, and blackspot.

* * * * *

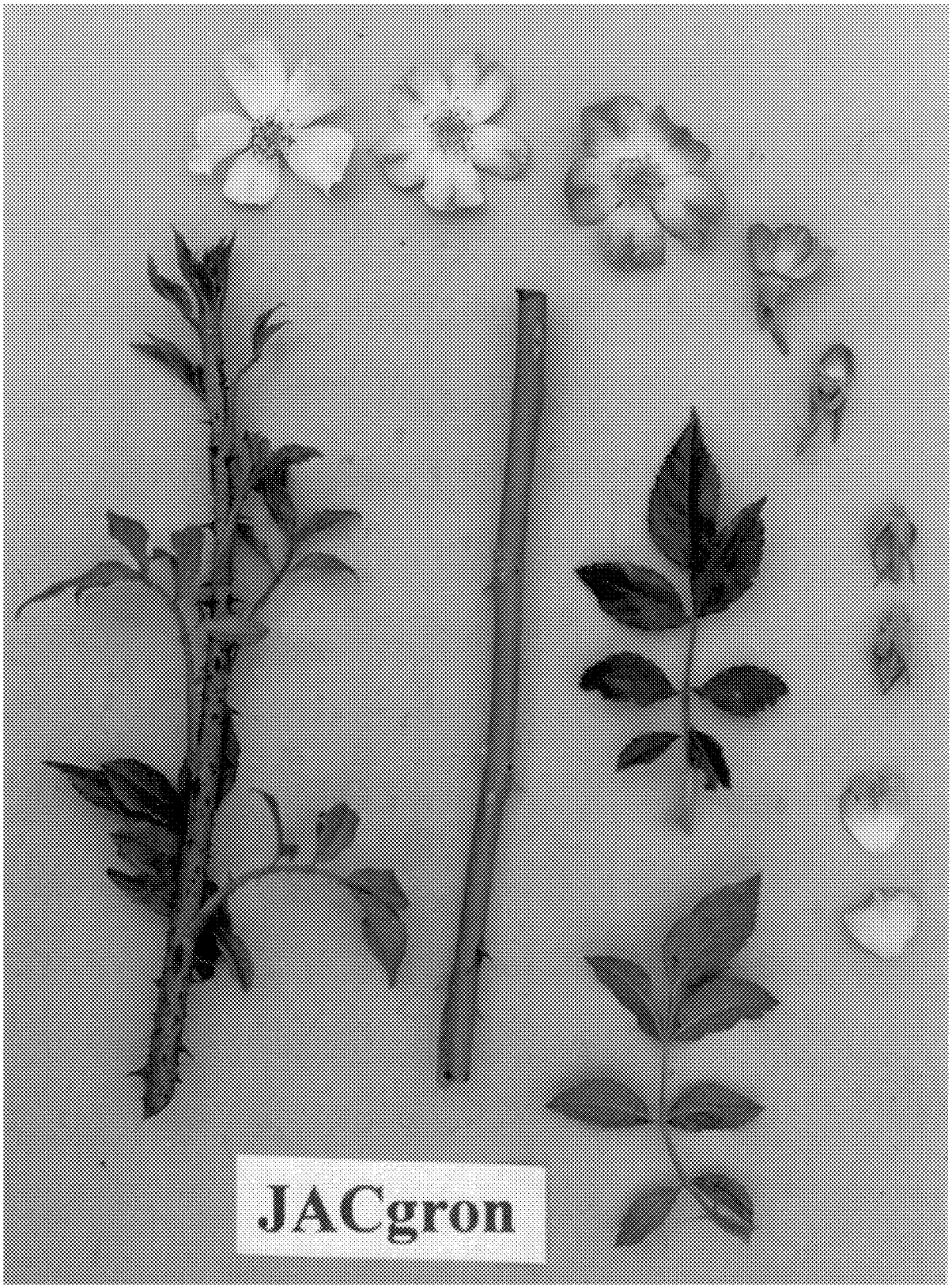
JACgron